United States Patent [19]

Cacho et al.

[11] Patent Number: 5,459,318
[45] Date of Patent: Oct. 17, 1995

[54] AUTOMATED FLUID BED PROCESS

[75] Inventors: Miguel A. Cacho; Ka H. Cheng, both of Lansdale, Pa.

[73] Assignee: McNeil-PPC-Inc., Milltown, N.J.

[21] Appl. No.: 241,940

[22] Filed: May 12, 1994

Related U.S. Application Data

[63] Continuation of Ser. No. 938,739, Aug. 31, 1992, abandoned.

[51] Int. Cl.$^6$ .................................................. G01N 21/35
[52] U.S. Cl. ................................. 250/341.2; 250/339.1; 250/339.11; 250/341.8
[58] Field of Search .................................. 264/40.2, 117; 425/222, 135; 250/341, 339; 356/445

[56] References Cited

U.S. PATENT DOCUMENTS

| | | | |
|---|---|---|---|
| 3,886,364 | 5/1975 | Walker et al. | 250/343 |
| 4,180,331 | 12/1979 | Lundstrom | 356/445 |
| 4,540,286 | 9/1985 | Satake et al. | 356/445 |
| 4,563,581 | 11/1986 | Perten | 250/341 |
| 4,595,833 | 6/1986 | Sting | 250/353 |
| 4,640,614 | 2/1987 | Roberts et al. | 250/341 |
| 4,698,190 | 10/1987 | Shibata et al. | 250/339 |
| 4,742,228 | 5/1988 | Bischoff | 250/341 |
| 4,852,028 | 7/1989 | Korpela | 364/567 |
| 4,910,403 | 3/1990 | Kilham et al. | 250/343 |
| 4,991,915 | 2/1991 | Thompson et al. | 324/640 |
| 5,003,174 | 3/1991 | Datwyler et al. | 250/341 |
| 5,007,740 | 4/1991 | Jeannotte et al. | 356/436 |
| 5,034,609 | 7/1991 | Satake et al. | 250/339 |
| 5,044,747 | 9/1991 | Anthony | 356/246 |
| 5,278,412 | 1/1994 | DeThomas et al. | 250/341 |

FOREIGN PATENT DOCUMENTS

| | | | |
|---|---|---|---|
| 1138528 | 6/1986 | Japan | 250/341 |
| 422783 | 9/1974 | U.S.S.R. | 356/445 |

OTHER PUBLICATIONS

S. Vemuri, "Measurement of Moisture Conent in Tablet Granulations", Pharmaceutical Technology, pp. 119–123, Sep. 1983.

R. J. Campbell, "Fluid Bed Process Control Based on Moisture Content", Vector Corporation, Marion, Iowa, undated.

*Primary Examiner*—Carolyn E. Fields
*Attorney, Agent, or Firm*—Bernard F. Plantz

[57] ABSTRACT

The present invention provides an apparatus and process for monitoring the moisture content of particulate material within a fluid bed apparatus such as a fluid bed granulator or fluid bed dryer. The apparatus comprising a probe with a conduit means for near infrared light wherein the end of the probe is positioned in the bowl of a fluid bed apparatus in a region of constant bulk density wherein said probe may be operably linked to a near infrared analyzer. A process for monitoring the moisture content of particulate material in a fluidized bed apparatus comprising irradiating a particulate material in a fluidized state with a constant bulk density with a near infrared light source, detecting the reflected near infrared light from the particulate material with a near infrared sensor and determining the moisture content by comparing the moisture content the sensor output with reference values for the moisture content for the particulate material and optionally adjusting the operating parameters of said fluidized bed apparatus in response to said moisture content.

13 Claims, 5 Drawing Sheets

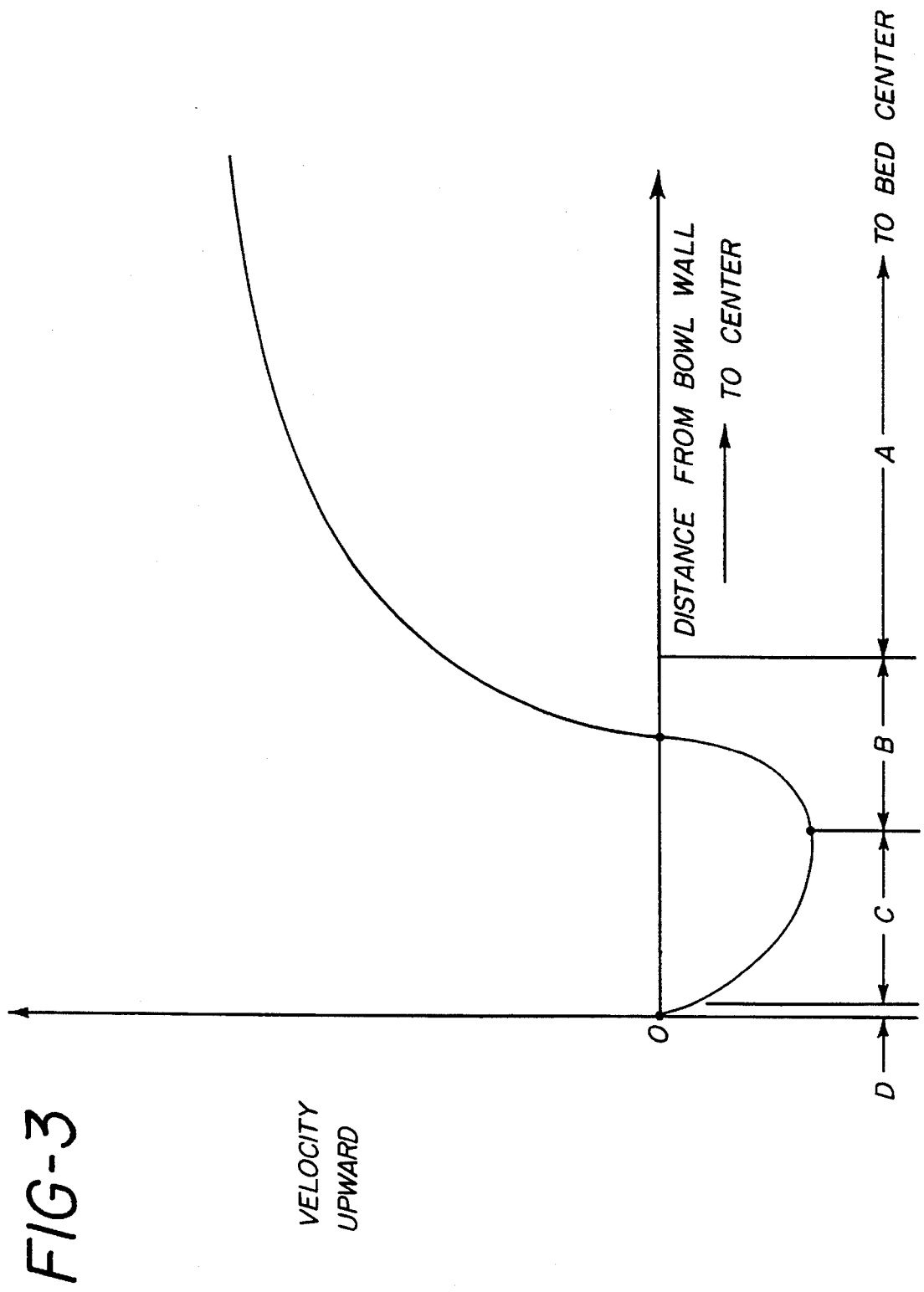

AUTOMATED FLUID BED PROCESS

This is a continuation of application Ser. No. 07/938,739, filed Aug. 31, 1992, now abandoned.

FIELD OF THE INVENTION

This invention relates to a probe and method of using said probe in a fluid bed apparatus with a near infrared moisture analyzer to monitor the moisture content of pharmaceuticals, foods and chemicals.

BACKGROUND OF THE INVENTION

Fluid bed granulation is being used increasingly in the pharmaceutical, food and chemical industries because of its special agglomeration capabilities. The pharmaceutical industry has been using fluid bed technology for more than ten years in the development and production of solid dosage forms.

A fluid bed granulator usually consists of a filter chamber, expansion chamber with one or more spray nozzles, product bowl and air inlet plenum. A fluid bed granulator operates by fluidizing a particulate material with air supplied from the air inlet plenum. Simultaneously a binding solution is sprayed onto the fluidized particulate material to facilitate the aggregation of individual particles into larger granules. The wet aggregates are dried by the fluidizing air in the granulator. The process is continued until the granules achieve the desired size.

During the granulation process, the moisture content of the granules should be monitored carefully. The moisture content is directly related to particle size, uniformity of the size distribution and build-up rate of the granules produced during the granulation process. Currently the moisture content of granules is monitored manually. The operator takes samples from the granulator at regular intervals and determines the loss of weight on drying the sample (LOD). The loss of weight is then correlated to the moisture content of the granules. The LOD test takes from 5–15 minutes to be performed depending on the product moisture. The operator will then analyze the moisture data and adjust the operating parameters accordingly. Since the LOD test is time consuming, the number of LOD tests that can be performed during granulation is limited. In addition there is always the inherent sampling error because of differing sample size and sample non-uniformity. The error prone and delayed information from the LOD test causes the granulation process to produce inconsistent and out of specification product on a regular basis.

Recently infrared and near infrared moisture analyzers have begun to replace the LOD test as the preferred method of determining moisture content. Although, using infrared and near infrared analyzers to measure the moisture content of samples significantly reduces the time delay in measuring the moisture content it does not eliminate sampling errors. Special precautions must be taken with infrared and near infrared moisture analyzers. Since these analyzers measure only surface moisture exposing samples to ambient conditions will result in significant errors in the measurement made by infrared or near infrared analyzers. As a solution to this problem, it has been suggested to locate an infrared or near infrared moisture sensor within the fluid bed granulator to provide on-line moisture content data.

However, the environment within a fluid bed granulator makes it very difficult to obtain accurate measurements of the moisture content with an infrared or near infrared moisture analyzer. If the sensor is placed flush with the wall of the product bowl a cake of noncirculating particulate material will block the infrared sensor. If the sensor is further into the product bowl, the turbulent flow of fluidizing air and particulate material will not have the necessary constant bulk density to provide a reliable reading.

Thus it would be a significant contribution to the art to provide a process and apparatus for facilitating the accurate measurement of the moisture content of the particulate material within a fluid bed apparatus. It would also be a significant advancement to the art to provide an apparatus and process which would allow for the moisture content of the particulate material of a fluid bed apparatus to be monitored and operating variables of the fluid bed apparatus to be adjusted in response thereto.

One object of the present invention is to provide an apparatus and process for monitoring the moisture content of the particulate material in a fluid bed apparatus.

Another object of the present invention is to provide an apparatus and process for monitoring the moisture content of the particulate material in a fluid bed apparatus and automatically adjusting operating variables in response thereto.

A further object of the present invention is to provide a near infrared probe suitable for use in a fluid bed apparatus.

These objects and other objects and several advantages provided by the present invention are presented in the following specification including the Figures, Examples and claims.

SUMMARY OF THE INVENTION

We have discovered in one embodiment of the present invention a process for measuring the moisture of particulate material in a fluidized bed which comprises (a) irradiating a particulate material in a fluidized state having a constant bulk density with a near infrared light source; (b) detecting the near infrared light reflected from said particulate material with a near infrared sensor; (c) determining the moisture content by comparing the infrared sensor output with reference values for the particulate material.

In another embodiment of the present invention, we have discovered a process for the automated operation of a fluid bed granulator comprising (a) measuring the moisture content of a particulate material with a constant bulk density in a fluid bed granulator; and (b) comparing the measured moisture content with a predetermined desired moisture content; then (c) controlling in response to said comparison, an operative parameter affecting the granulation.

In a further embodiment of the present invention, we have discovered an apparatus suitable for use as a probe for a near infrared analyzer and attachment to a fluidized bed apparatus having a bowl with a port comprising a support base with an aperture; a conduit means for near infrared light having a first end and a second end, the first end being mounted on said base over the aperture so that optical communication is provided through said aperture; the second end extending within the bowl a distasnce β from the bowl wall to a region of constant bulk density in a fluidized bed granulation or a fluidized bed dryer when the support base is attached to the bowl of said fluidized bed apparatus; a window for covering the second end of the conduit means for near infrared light, said window being transparent to near infrared light, the window having an outer surface; the outer surface of said window being disposed at an angle sufficient to avoid the occlusion of said window during the operation of a fluid bed apparatus.

BRIEF DESCRIPTION OF THE FIGURES

FIG. 3 is a diagram of the velocity profile of particulate material across the bowl of a conventional fluid bed apparatus.

DETAILED DESCRIPTION OF THE INVENTION

The present invention provides a process and apparatuses for monitoring the moisture content of particulate material within a fluid bed granulator or fluid bed dryer hereinafter referred to as a fluid bed apparatus. For the purposes of illustration, FIGS. 1–6 present only a diagram of a fluid bed granulator. Fluid bed granulators and fluid bed dryers operate in very similar manners. The primary difference being that fluid bed dryers do not utilize sprays to agglomerate particles. Accordingly, the present invention provides a process and apparatuses which may be used with either a fluid bed granulator or fluid bed dryer.

Figure 1:
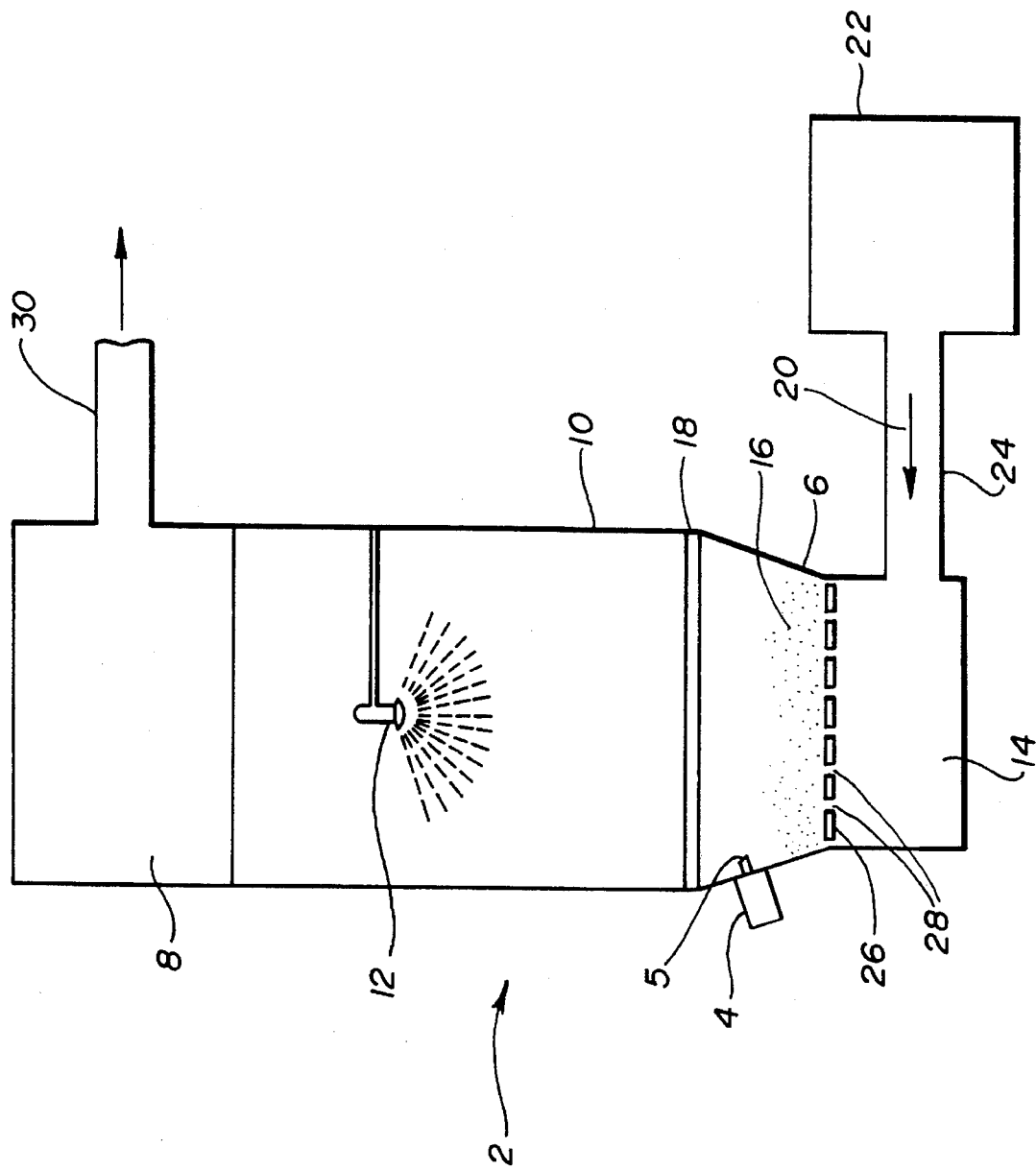
FIG. 1 is a diagrammatic view of the inventive fluid bed granulator with a NIR sensor and probe attached to the bowl of a fluid bed granulator.

FIG. 1 diagrammatically illustrates a conventional fluid bed granulator 2 having attached thereto a near infrared moisture analyzer 4 and the inventive probe 5. The probe is positioned in the product bowl 6 of the fluid bed granulator 2. The probe 5 is a conduit means for near infrared light. The fluid bed granulator shown in FIG. 1 is a top spraying granulator but this invention may be utilized with other spray configurations such as side spraying fluid bed granulators.

In the operation of a fluid bed granulator 2, process air 20 is supplied by an air handling means 22 which is in gaseous communication with the air inlet plenum 14 by a suitable conduit means for process air 20. The air handling means 22 provides a means for regulating the supply, the temperature and optionally the humidity of the process air 20 supplied to the air inlet plenum 14.

The process air 20 supplied to the air inlet plenum 14 passes through grid 26 via grid ports 28. As the process air 20 exits grid ports 28 it enters bowl 6 and contacts the particulate material 16. The process air 20 is supplied in a sufficient quantity through grid ports 28 to fluidize the particulate material 16. As a result of the fluidization a portion of particulate material 16 will be lifted by the process air 20 into the expansion chamber 10. As the process air 20 enters the expansion chamber 10 it expands which reduces the process air's 20 density and consequently the process air's 20 lifting capacity. The process air 20 then pass through filter chamber 8 which removes any dust entrained in process air 20 and the process air 20 exits the fluid bed granulator by exhaust port 30.

The particulate material 16 while in expansion chamber 10 is sprayed with a liquid from one or more spray nozzles 12. The liquid sprayed unto the particulate material 16 promotes the agglomeration of individual particles by collision and adhesion into aggregate particles (which will also be referred to as particulate material). As a result of the reduced lifting capacity of the expanded process air 20, the particulate material 16 begins to fall back towards periphery of bowl 6.

Figure 2:
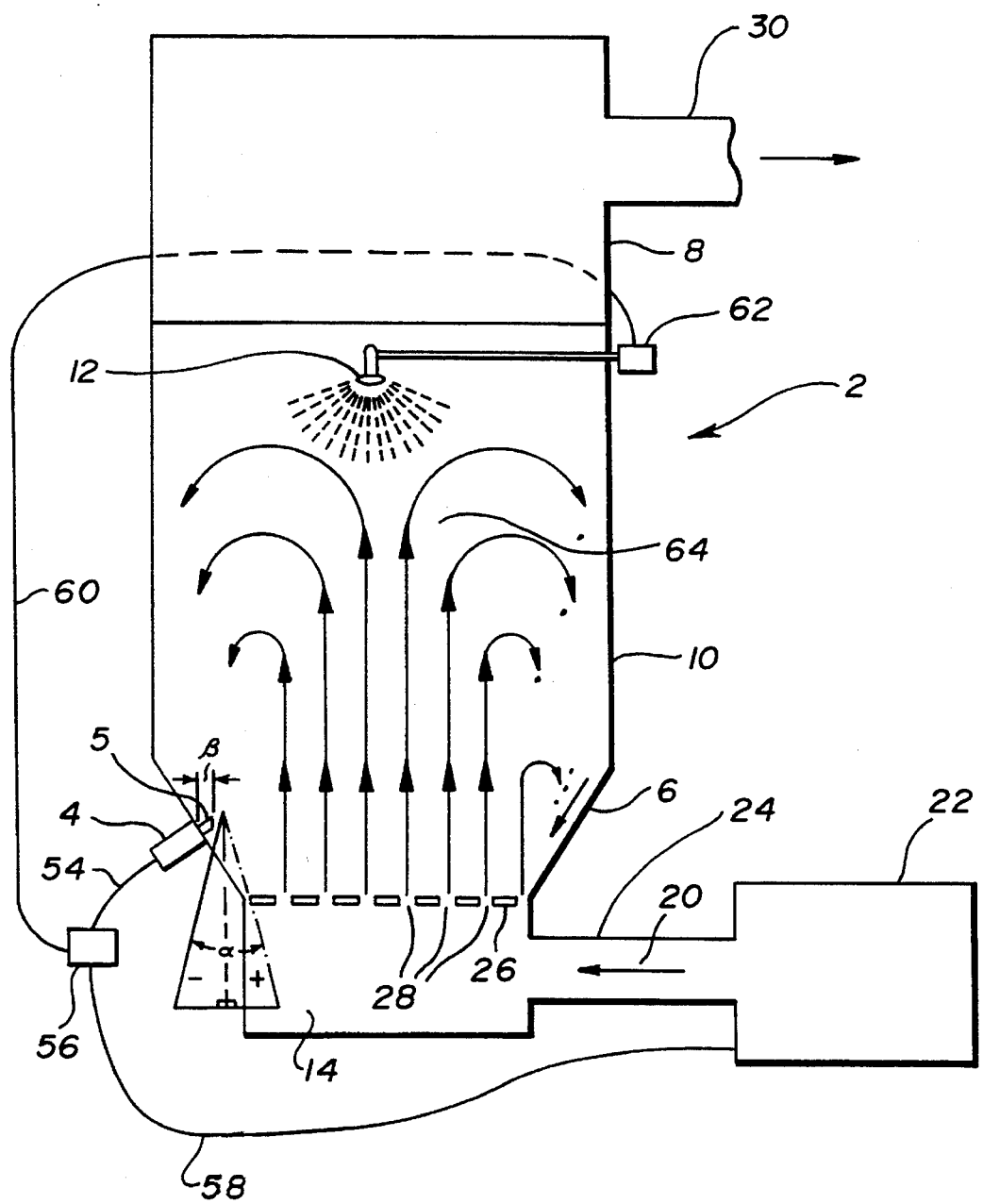
FIG. 2 is a diagrammatic representation of an automated fluid bed granulator with the probe within the bowl of the fluid bed granulator. This figure also illustrates the flow pattern of particular material within a fluid bed apparatus.

The general circulation pattern of the fluidized particulate materials 16 is diagrammatically illustrated in FIG. 2. As is illustrated by arrows 64, the particular material 16 rises in the center of the bowl 6 and fall back towards the grid 26 about the periphery of the bowl 6.

To provide optimal circulation of the fluidized particulate materials within a fluid bed apparatus, the grid 26 should have very few grid ports 28. The grid ports 28 should be uniformly distributed throughout the grid 26 to completely fluidize the particulate material. The grid 26, the grid ports 28 and the process air 20 should be adjusted to avoid cold spots, surging and channeling of the particulate material 16.

Referring to FIG. 2 and FIG. 3, the representation of the circulation pattern 64 and velocity profile for a fluidized bed apparatus will generally correspond to those shown in FIG. 2 and FIG. 3 when a sufficient quantity of air is being supplied to fluidize the particulate material 16 within the bowl 6.

Measuring the moisture content of a particulate material within a fluidized bed requires the correct placement of the probe 5. Probe 5 must be placed in a region within the fluidized bed apparatus where the bulk density of the particulate material is substantially constant and is representative of the current moisture content of the particulate material within the fluidized bed apparatus. Constant bulk density for the purpose of this invention can be defined as a substantially uniform distribution of particulate material in a unit volume.

Constant bulk density does not exist in areas of the fluidized bed apparatus where the process air 20 is passing through grid ports 28 into the particulate material 16 because of the continual formation of air bubbles or void volumes. Region A of FIG. 3 corresponds to the turbulent fluidized region of a fluidized bed apparatus when bubbles form. This region is characterized by an average positive velocity of the particulate material away from grid 26. Region B of FIG. 3 also corresponds to a transition region of the fluidized bed when the bulk density is not constant over time.

Region C and D of FIG. 3 correspond to regions of a fluidized bed apparatus which have a constant bulk density. Regions C and D generally correspond to regions of a fluidized bed apparatus where the particulate material 16 has a negative velocity. Region D, however, is a region where the velocity of the particulate material is at or close to zero. Region D is representative of a cake-like layer which often forms on the inside surface of a fluidized bed apparatus. In Region D, the particulate material is insulated from the dynamic changes occurring in the remaining regions of the fluid bed. Consequently, measurements of moisture in Region D are unsuitable for monitoring the moisture content of a fluid bed apparatus.

Region C of FIG. 3 provides the combination of a constant bulk density while being representative of the moisture content of most of the particulate material in a fluidized bed apparatus. Accordingly, probe 5 should extend a distance $\beta$ into Region C. Region C can be located empirically in a fluidized bed apparatus by plotting a velocity profile of the particular material and observing the particulate materials bulk density. Generally, Region C will exist from ½" to 5" (1.3 to 12.7 cm) from the wall of the bowl 6. Region C may be narrower and even may cease to exist as the measurements are taken on progressively lower positions on the bowl 6 closer to grid ports 28. Therefore, probe 5 should be place preferably at least ¼ the height of the bowl 6 from the grid 26 and most preferably at least ½ the height of the bowl from grid ports 28.

Figure 4:
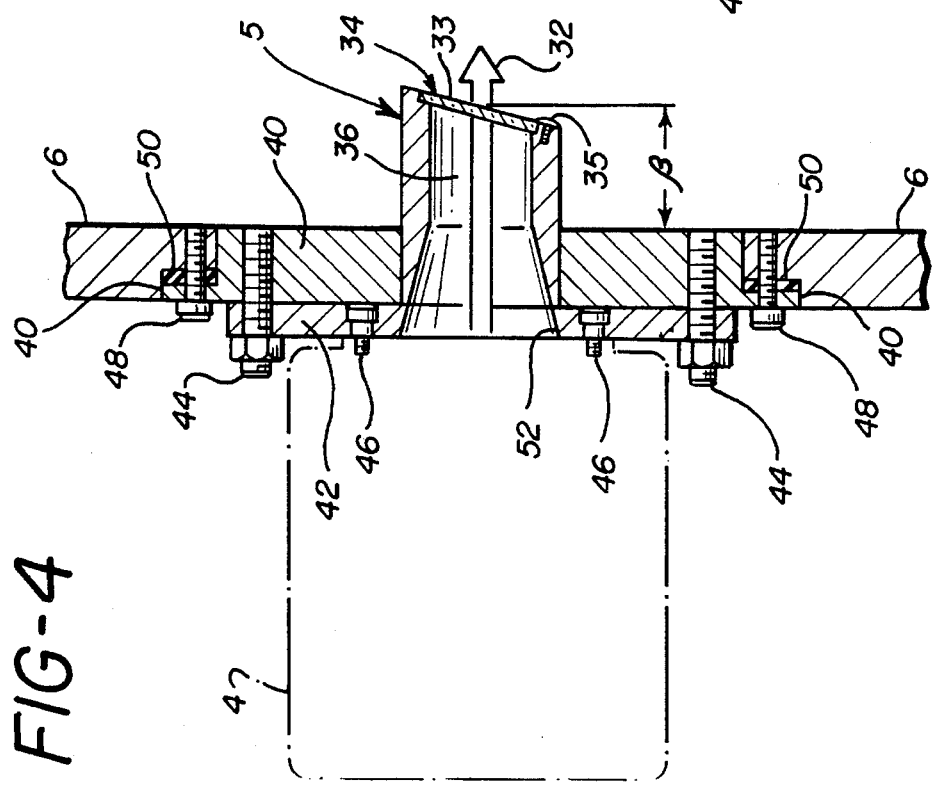
FIG. 4 is a diagrammatic representation of a side elevation of the inventive NIR probe.

To assure that the reading obtained from the near infrared analyzer is accurate care must be taken to avoid occlusion of the window 34 by a layer of caked on particulate material or particulate material which is no longer circulating. As illustrated in FIG. 2 and FIG. 4, the window 34 of probe 5 should be disposed at an angle α which represents an angle in the range of from about +10 to about −10° with respect to a vertical line perpendicular to the plane of grid 26.

Figure 5:
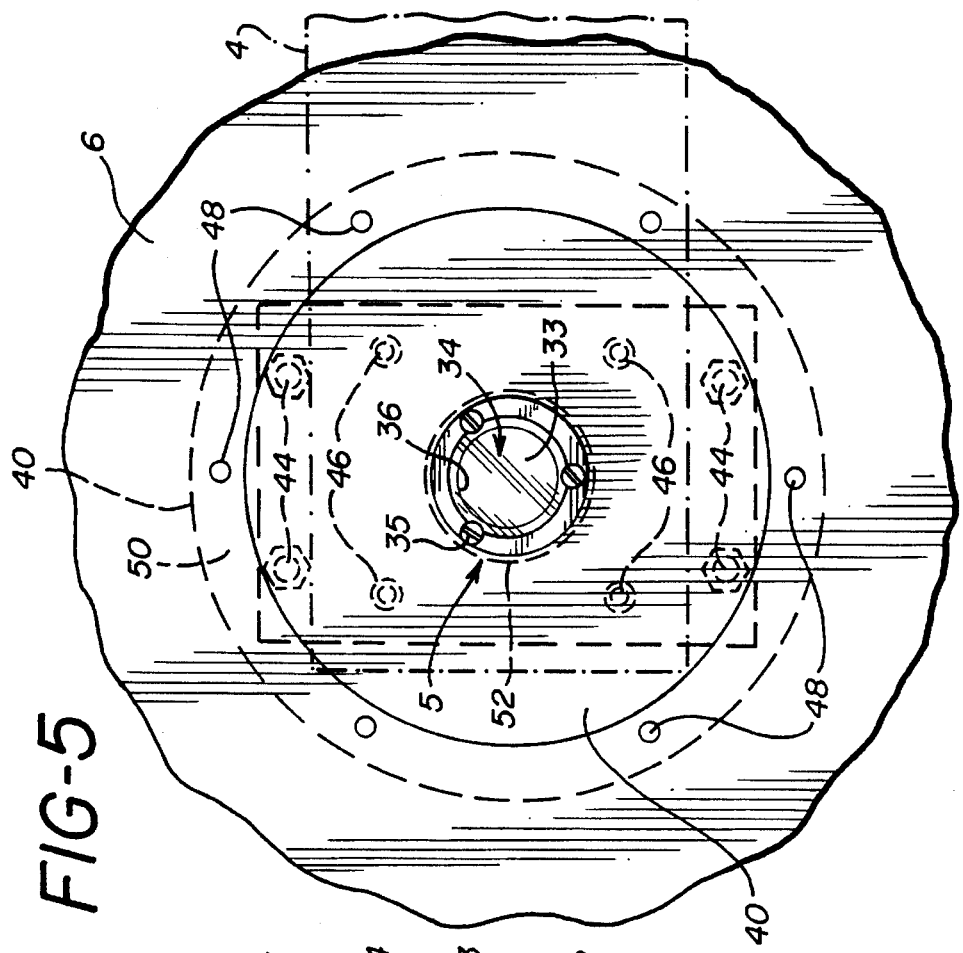
FIG. 5 is a diagrammatic representation of the retaining plate and support flange for the NIR probe of FIG. 4.

The probe 5 which is a conduit means for near infrared light may be of any appropriate material or materials which provides a path for near infrared light 32 from the near infrared moisture analyzer 4 to the particulate material 16 in Region C of a fluid bed apparatus. Probe 5 can be secured to the bowl of a fluid bed apparatus by any appropriate means such as illustrated in FIG. 4 and FIG. 5. Probe 5 could also be permanently attached to bowl 6 by welding. FIG. 4 and FIG. 5 provide one preferred embodiment of the present invention.

With reference to FIG. 4 and FIG. 5 the near infrared moisture analyzer 4 is attached to the probe 5 by a means for attaching such as retaining bolts 46. The alignment of probe 5 and moisture analyzer 4 is such as to provide for the transmission and reception of near infrared light 32 by the near infrared moisture analyzer 4 to the external surface 33 of window 34. Aperture 52 of support base 42 is therefore aligned with the near infrared moisture analyzer 4 to permit the transmission and reception of near infrared light. Similarly conduit means for near infrared light 36 is also aligned and disposed with window 34 and aperture 52 to provide a path for the transmission and reception of near infrared light. Window 34 is secured to conduit means 36 by window retaining means 35. The aperture 52 and conduit means 36 are secured in place by retaining means such as flange bolts 44. Flange bolt secures the flange 40 to support base 42. Flange 40 is secured to bowl 6 by a suitable retaining means such as bowl retaining bolts 48. Retaining bolts 48 mate flange 40 to the bowl to provide an air-tight seal.

Aperture 52 and the first end of the conduit means 36 in contact therewith, may optionally have a larger cross-section area than the second end of the conduit means to which the window 34 is affixed. The larger cross-sectional areas should be disposed to provide for the increased reception of near infrared light reflected from particulate material 16 in bowl 6. One suitable arrangement is to uniformly increase the cross-section area to provide a conical surface from approximately ½ the length B of the conduit means through aperture 52. As previously mentioned, the length of the conduit means 36 should be determined empirically to extend window 34 into a region where the bulk density of the particulate material 16 is constant during the operation of the fluid bed apparatus and the particulate material is constantly moving to provide an accurate representation of the moisture content of the particulate material in the fluid bed granulator. Although the operating conditions and placement of the probe 5 may alter the distance β the second end of the conduit means 36, to which the window 34 is affixed, is spaced from the bowl wall, generally this distance will be a perpendicular distance in the range of from about ½" to about 5" (1.3 to 12.7 cm) from the bowl of the fluid bed apparatus to the center of window 34 and more preferably from 1" to 4" from the wall of the bowl when the probe 5 is placed at least ¼ and preferably at least ½ the height of the bowl from grid 26.

In operation the near infrared analyzer will emit near infrared light which will travel down the conduit mean 36 through window 34 and strike particulate material 16. A portion of the near infrared light will be reflected back through window 34 travel down conduit means 36 and be measured by a near infrared analyzer sensor. The near infrared moisture analyzer will then provide an output value for the moisture content of a given particulate material. These output values may be correlated to a particular moisture content for a particular particulate material. Generally, it is assumed that the moisture content measurement vary linearly. However, in actuality the output of a near infrared moisture analyzer does not have a linear correlation with moisture content. Therefore, it is advisable to calibrate the moisture analyzer by taking multiple readings of a particular particulate material having a determined moisture content and correcting for non-linearity using a curve correcting formula.

The output from the near infrared analyzer 4 can be supplied to a microcomputer or central processing unit 56 (hereinafter microcomputer) through a conduit means for output 54. The microcomputer 56 will correlate the output from the analyzer with stored values to determine the actual moisture content of the particulate material 16. The microcomputer 56 will then compare the actual moisture content of the particulate material with a stored value for the desired end point moisture content. If the end point moisture content has been reached, the process being performed in fluid bed apparatus is signal as complete or is stopped by a signal or signals from microcomputer 56. Otherwise the actual moisture content is compared to an optimal setpoint for the moisture content for process being performed in the fluid bed apparatus. If the actual moisture content does not equal the optimal setpoint the microprocessor calculates optimal settings for the operating parameters of the fluid bed apparatus (such as the air flow rate, air temperature, differential pressure across the product, etc...) and the calculated optimal setting are then signaled to one or more appropriate operating parameter controls means. The operating parameters for fluid bed apparatuses are well known to those skilled in the art such as the differential pressure across the product which is the difference in air pressure between the air pressure measured in the air inlet plenum 14 and in expansion chamber 10. Similarly, methods and formulas for calculating optimal setting for the operation of fluid bed apparatuses are also well known in the art. If the optimal setpoint was equal to the actual moisture content, the process continues and another moisture reading is taken. The process of measuring and comparing continues until the end point is reached.

Figure 6:
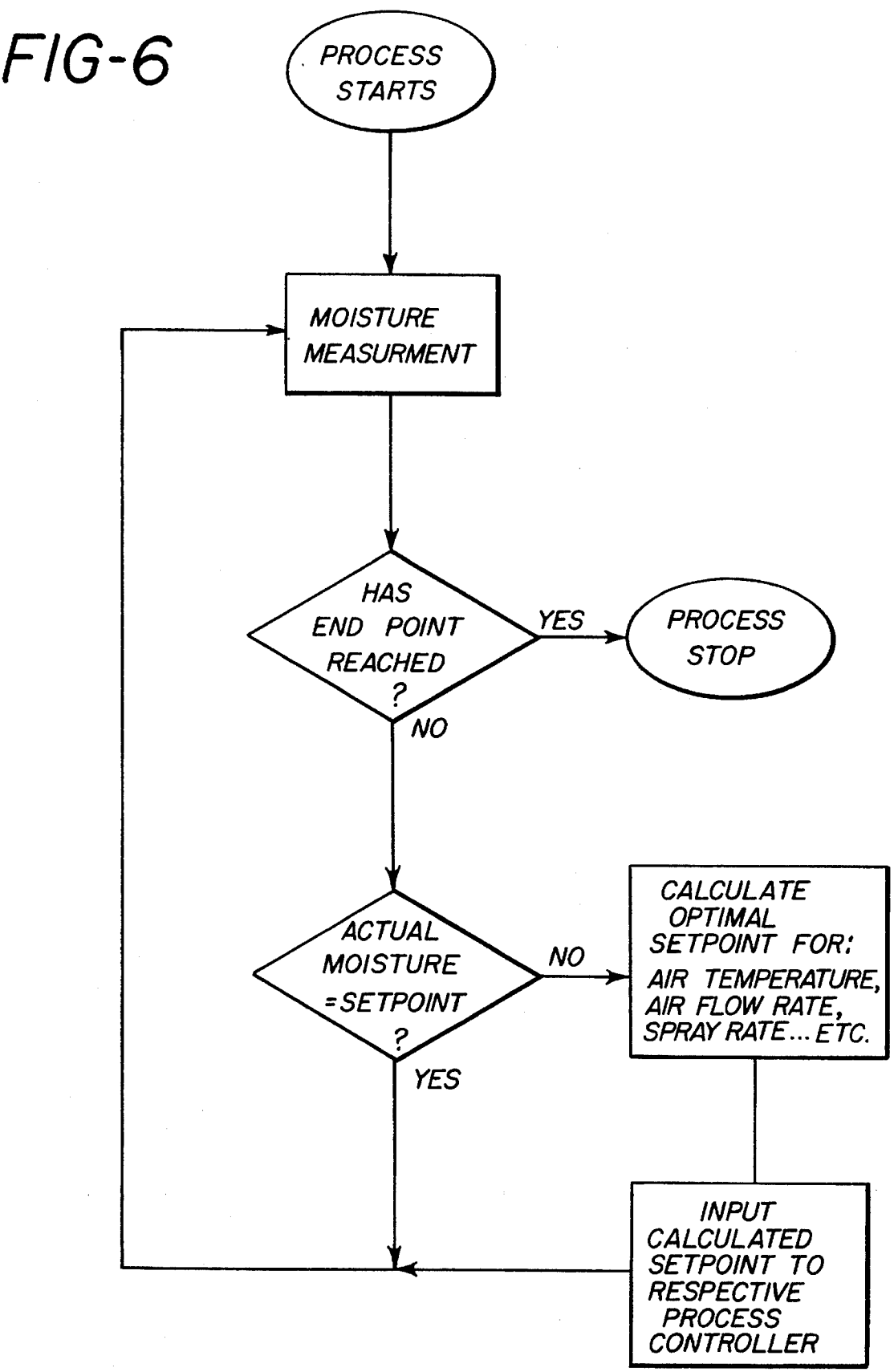
FIG. 6 is a schematic representation of the inventive control system for a fluid bed granulator.

FIG. 2 and FIG. 6 illustrate a apparatus and process suitable for a fluid bed granulator. As is indicated by FIG. 2, the moisture analyzer 4 provides an output signal to the microcomputer 56 via signaling means 54. The microcomputer then correlates the output from the moisture analyzer with stored values to determine the actual moisture content. The actual moisture content is compared first to the end point moisture value. If the values are equal or the actual moisture content exceeds the end point moisture content, the process is signaled to be stopped. The microcomputer may signal the need to stop the process to the operator and/or stop the process by signalling the air handling unit 22 via means for signalling 58 and the control means for the spray nozzles 62 to shut off via means for signalling 60.

If the fluid bed granulation process has not reached the end point moisture value, the actual moisture content is compared to an optimum moisture content. If the actual moisture content is equal to the optimum moisture content, the granulation process continues and another moisture measurement is made. Otherwise, the microcomputer calculates an optimal setting for one or more of the operating parameters such as the air temperature, air flow rate, pressure differential across the product and the liquid spray rate from the spray nozzles. These values are then signalled to the controller within the air handling unit 22 via means for signalling 58 and the control means for the spray nozzles 62 via means for signalling 60. The granulation process continues, another measurement of the moisture content is performed and the values compared until the end point is reached.

The microcomputer 56 may also print out the output from the moisture analyzer, actual moisture values and setting of the operating parameter control means including but not limited to the air handling unit 22 and the spray nozzle controller at desired intervals.

What is claimed is:

1. An apparatus for continuously monitoring the moisture content of a particulate material in a fluidized bed apparatus having a horizontal grid comprising:

a near infrared analyzer;

an optical conduit means having a first end and second end, said first end and second end being in optical communication with the near infrared analyzer;

a window made of a material transparent to near infrared light, said window positioned at the second end of the optical conduit means; and means for positioning said window at an angle relative to said grid to avoid the occlusion of said window by said particulate material during the operation of said fluidized bed apparatus and in a reqion in which said fluidized particulate material has a constant bulk density.

2. An apparatus in accordance with claim 1 wherein the optical conduit means has an inner diameter at each of said first end and said second end, wherein the inner diameter of the first end is larger than the inner diameter of the second end.

3. An apparatus in accordance with claim 1 wherein there is provided a means for attaching the optical conduit means to a fluid bed apparatus.

4. An apparatus in accordance with claim 1 wherein the near infrared analyzer provides an output to a microcomputer having a means to compare the output with one or more stored values and a means to signal the results of the comparison.

5. An apparatus in accordance with claim 1 wherein said angle is within the range of from about +10° to about −10° with respect to a vertical line perpendicular to said horizontal grid.

6. A probe for a near infrared analyzer suitable for attachment to a fluidized bed apparatus having a bowl for containing particulate material in a fluidized state and said bowl having a wall, said probe comprising:

a support base having an aperture;

means for attaching said support base to said bowl so that said aperture is in optical communication with said particulate material;

a conduit means for near infrared light having a first end and a second end, said first end being mounted on said support base in optical communication with said aperture, and said second end extending within said bowl a distance β from the bowl wall to a region in which said particulate material has a constant bulk density and which is free of any cake-like layer of said particulate material;

a window positioned at the second end of said conduit means, said window being transparent to near infrared light; and means for positioning said window such that the occlusion of said window during the operation of the fluidized bed apparatus is avoided.

7. An apparatus in accordance with claim 6 wherein the distance β is from about 1.3 cm to about 12.7 cm.

8. An apparatus in accordance with claim 6 wherein the support base has a means for operatively connecting said probe to a near infrared analyzer.

9. A fluidized bed apparatus, comprising:

a bowl for containing particulate material in a fluidized state, said bowl having a wall;

a near infrared analyzer;

an optical conduit means having a first end and a second end, said first and second ends being in optical communication with said near infrared analyzer, and said second end extending within said bowl a distance β from the bowl wall to a region in which said fluidized particulate material has a constant bulk density and which is free of any cake-like layer of said particulate material; and a window covering said second end of said conduit, said window being transparent to near infrared light and being disposed at an angle to avoid the occlusion of said window during the operation of said apparatus.

10. A fluidized bed apparatus of claim 9 wherein the distance β is from about 1.3 cm to about 12.7 cm.

11. The fluidized bed apparatus of claim 9 wherein the optical conduit means has an inner diameter at each of said first end and said second end, and the inner diameterof said first end is larger than the inner diameter of said second end.

12. A fluidized bed apparatus of claim 9 further comprising a microcomputer, said near infrared analyzer providing an output to said microcomputer, and said microcomputer having a means to compare the output with one or more stored valves, and a means to signal the results of the comparison.

13. A fluidized bed apparatus of claim 9 wherein said region is representative of the current moisture content of said particulate material within said apparatus.

* * * * *